United States Patent [19]
Werning et al.

[11] Patent Number: 5,840,551
[45] Date of Patent: Nov. 24, 1998

[54] METHOD OF PRODUCING L-AMINO ACIDS BY FERMENTATION

[75] Inventors: Holger Werning, Duisburg, Germany; Harald Voss, Gratkorn, Austria; Walter Pfefferle, Halle; Wolfgang Leuchtenberger, Bielefeld, both of Germany

[73] Assignee: Degussa Aktiengesellschaft, Germany

[21] Appl. No.: 769,437

[22] Filed: Dec. 19, 1996

[30] Foreign Application Priority Data

Dec. 19, 1995 [DE] Germany ..................... 195 47 361.2

[51] Int. Cl.⁶ ..................... C12P 13/04; C12P 13/08; C12P 13/06
[52] U.S. Cl. ................. 435/106; 435/109; 435/113; 435/115; 435/116; 435/170; 435/830; 435/832; 435/840; 435/843; 435/872
[58] Field of Search ........................... 435/106, 115, 435/116, 109, 113, 170, 840, 843, 830, 832, 872

[56] References Cited

PUBLICATIONS

Derwent Abstract Biotech ABS 90–00963 Schendel et al Abstr. Pap. Am Chem. Soc. (1989) 198 Meeting.
Derwent Abstract WPIL 93–228506/29 Bachmann et al Abs of EO–551614 (Jul. 21, 1993).

*Primary Examiner*—Herbert J. Lilling
*Attorney, Agent, or Firm*—Cushman Darby&Cushman IP Group of Pillsbury Madison & Sutro LLP

[57] ABSTRACT

A method of producing L-amino acids by fermentation. Microorganisms of the genus Corynebacterium which exhibit an auxotrophy relative to an amino acid are used as biocatalysts. The method is characterized in that the carbon source on the one hand and the limiting amino acid on the other hand are fed in two or more different infeed currents to the process. The infeed profiles have, for example, a concave (saccharose) and an exponential (amino acid) form or a convex (saccharose) and likewise a convex (amino acid) form, with specific differing degrees of increase of the currents relative to each other over time.

12 Claims, 3 Drawing Sheets

METHOD OF PRODUCING L-AMINO ACIDS BY FERMENTATION

CROSS-REFERENCE TO RELATED APPLICATIONS

This application is based on German patent application no. 19547361.2 filed Dec. 19, 1995, the entire content of which is incorporated hereinto by reference.

BACKGROUND OF THE INVENTION

1. Field of the Invention

The invention relates to an improved method of producing L-amino acids by fermentation.

2. Background Information

Aside from a number of other amino acids, there is a great need in the feed [animal food] and foodstuff industries, for example, for L-lysine as an essential amino acid. The industrial production of, for example, L-lysine by fermentative methods with microorganisms is known. In general, auxotrophic mutants of *Corynebacterium glutamicum* are used. These mutants require one of the following nutrients for growth: Leucine or isoleucine, homoserine, threonine or threonine with methionine. They are then capable of forming large amounts of L-lysine.

Customary batch-fed processes are therefore controlled in such a manner that in addition to other nutrients and trace elements both the growth-limiting amino acid as well as the carbon source necessary for the formation of L-lysine are continuously fed in.

It has now been discovered that this process, in which the C-source such as, for example, saccharose and the limiting amino acid(s) are fed in during the growth- and fermentation phase in a concentration ratio which is constant to each other, results in the formation of undesired byproducts and in the foaming of the fermentation broth during the process.

At the same time, a way was sought of increasing the productivity and the reactor capacity.

SUMMARY OF THE INVENTION

The invention has as subject matter a method of producing L-amino acids by the fermentation of microorganisms excreting L-amino acids which microorganisms have an auxotrophy in relation to at least one other amino acid, which method is characterized in that the carbon source necessary for the growth and the formation of L-amino acid on the one hand and an amino acid or amino acids limiting the growth and the formation of amino acid together with an adequate amount of other nutrients and trace elements on the other hand are charged in two or more separate but chronologically simultaneously beginning inflow currents with chronological infeed profiles of differing form, which charging preferably does not take place in proportional amounts.

In a preferred embodiment the inflow current containing the limiting L-amino acid(s) has an exponential form in the graphic representation; however, the inflow current containing the carbon source has a profile which is concave in relation to the time axis, in particular beginning with a sharp rise located prior to the concave profile.

In a further embodiment the following picture results, namely, that the inflow current containing the limiting L-amino acid exhibits a rise in the graphic representation corresponding to a convex form and the inflow current containing the carbon source exhibits a profile which is concave relative to the time axis, both of which profiles exhibit a differing rise until the end of the fermentation in the sense that the rise of the infeed of the carbon source is greater, as is generally true.

A further variant is distinguished in that the inflow current containing the limiting L-amino acid exhibits a convex form and the inflow current containing the carbon source also exhibits a profile which is convex relative to the time axis, both of which profiles exhibit differing degrees of increase.

The combination of a linearly falling infeed rate of the carbon source with a convexly running inflow current of the limiting amino acid has proven to be favorable.

The L-amino acids to be produced are compounds from the group corresponding to claim 6, especially L-lysine.

Microorganisms used in the production stem from genera similar to those cited in claim 7.

The procedure described is preferably used for the fermentation of L-lysine using microorganisms of the genera Corynebacterium, Brevibacterium, Arthrobacter, Microbacterium, Bacillus or Nacordia excreting these amino acids.

In a special embodiment of the invention, a high L-lysine productivity is achieved especially in the case of auxotrophic strains of *Corynebacterium glutamicum* in the framework of a semi-continuous fermentation, if adjustment is made for a specific product-formation rate of 0.06 $h^{-1}$ to 0.25 $h^{-1}$.

According to the method of the invention microorganisms of the genera Corynebacterium, Brevibacterium, Arthrobacter, Microbacterium, Bacillus or Nacordia can be used for the fermentative production of L-lysine which behave auxotrophicly vis-à-vis one or several of the L-amino acids leucine, homoserine, threonine, methionine, isoleucine and are resistant to feedback inhibition and/or repression by at least one of the compounds lysine and lysine analogues, threonine and threonine analogues and isoleucine and isoleucine analogues.

An advantage of the strategy of the method of the invention over known methods with only one inflow current is the significant increase in the productivity of the microorganisms, especially for example as regards L-lysine.

A comparison of the volumetric productivities (see examples) leads to an improvement of >50%. Even the calculation of the reactor capacity, performed independently of the degree of filling, shows its elevation by >10%.

DETAILED DESCRIPTION OF THE INVENTION

EXAMPLES

Example 1

This process explains the course of the processing of an L-lysine fermentation with an especially high reactor capacity:

The strain *Corynebacterium glutamicum* DM282-2 is grown to 2 l inoculum in two propagation stages. To this end, a culture medium is used in each instance which contains 1.92% sacaharose, 4.19% molasses, 11.55% soy meal hydrolysate, 3.05% ammonium sulfate, 0.58% urea, 0.024% magnesium sulfate heptahydrate, 0.05% $KH_2PO_4$, 0.06% citric acid monohydrate, 0.00096% iron(II) sulfate heptahydrate, 0.00096% manganese(II) sulfate monohydrate, 0.00577% L-leucine, 0.00385% L-threonine, 0.0077% L-methionine, 0.000038% D-biotin, 0.19% thiamine.HCl and 0.96% Nalco. The pH is adjusted to 6.8 with NaOH. A propagation fermentation is inoculated with the inoculum obtained in this manner which contains 300 l of the fermentation medium M1. This medium consists of 0.51% molasses, 7.69% saccharose, 5.69% zein [gluten of maize] hydrolysate, 1.15% ammonium sulfate, 0.0029% manganese(II) sulfate monohydrate, 0.072% magnesium sulfate heptahydrate, 0.0029% iron(II) sulfate heptahydrate, 0.001923% calcium chloride dihydrate, 0.0015% zinc sulfate heptahydrate, 0.000014% copper sulfate heptahydrate, 0.0577% citric acid monohydrate, 0.01% $H_3PO_4$, 0.000029% D-biotin, 0.000019% thiamin HCl, 0.096% Nalco, 0.000048% ferrioxamine E, $FeCl_3$. This mixture is cultivated approximately 20 hours at 30° C., pH 7.0 and a controlled $pO_2$ of at least 15%. A biomass concentration of approximately 10 g/l is achieved thereby. The production fermenter, which contains 4000 l medium M1, is now inoculated with these 300 l fermentation broth from the propagation fermentation. This fermentation is carried out at 33° C., pH 7.1 and $pO_2$>15% until the achievement of an optical density of OD 30.

Then, an increase of temperature to 35° C. and of the pH to pH 7.5 takes place with the start of the infeed.

Figure 1:
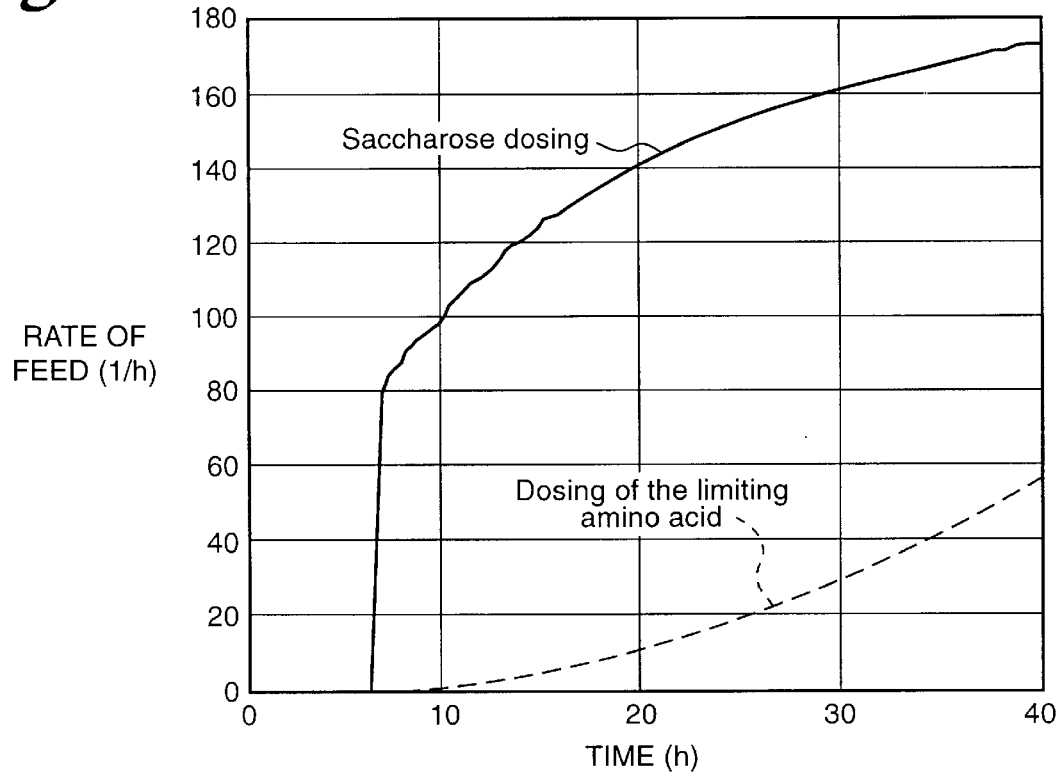
FIG. 1. Timecourse of charging infeed media M2.1 (saccharose) and M2.2 (amino acid) in Example 1.

The infeed media M2.1 and M2.2 are charged as shown in FIG. 1. Infeed medium M2.1 (saccharose dosing) consists of a saccharose solution of 600 g/l and infeed medium M2.2 (amino acid dosing) of a solution containing 15 g/l limiting amino acid and the above-mentioned mineral additives and additive substances in an adequate amount.

Example 2

This process explains the course of the processing of an L-lysine fermentation with especially high productivity of the microorganisms as concerns L-lysine:

The medium composition and the inoculation procedure takes place as in example 1. This fermentation is carried out at 33° C., pH 7.1 and $pO_2$>15% until an optical density of OD 30 is achieved.

Then, an increase of the temperature to 35° C. and of the pH to pH 7.5 takes place with the start of the infeed.

Figure 2:
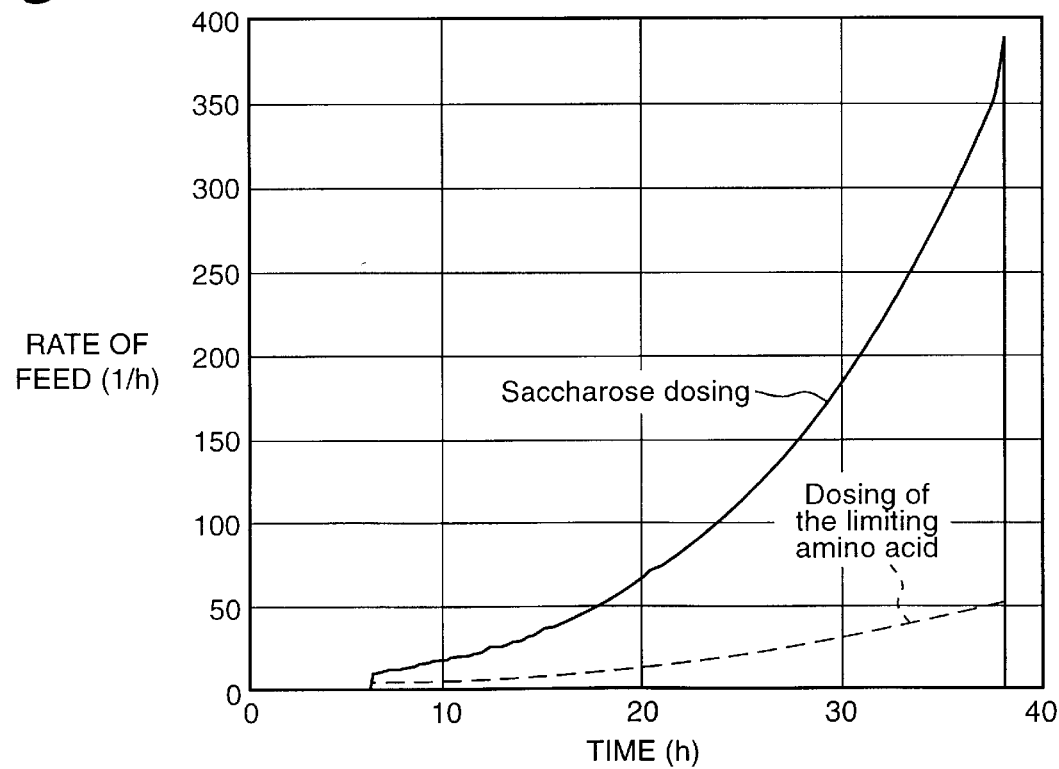
FIG. 2. Timecourse of charging infeed media M2.1 (saccharose) and M2.2 (limiting amino acid) in Example 2.

The infeed media M2.1 and M2.2 are charged as shown in FIG. 2. Infeed medium M2.1 (saccharose dosing) consists of a saccharose solution of 600 g/l and infeed medium M2.2 (amino acid dosing) of a solution containing 15 g/l limiting amino acid and the above-mentioned mineral additives and additive substances in an adequate amount.

Example 3

This example contains the comparison with a standard test in which the carbon source and the limiting amino acid (L-leucine) are fed in one current.

The media basically correspond, as well as the other measures of the method, to those in examples 1 and 2.

| Parameters | 941147 standard with 1 inflow | 941177 in accordance with the invention |
|---|---|---|
| inoculum (1) | 0.38 | 0.38 |
| start volume (1) | 5.78 | 2.78 |
| inflow medium (1) | 2.64 (sugar + supplements) | 2.13 (sugar) (M 2.1) |
| saccharose consumed in g | 2058 | 2317 |
| inflow medium 2 (1) | — | 0.86 (supplements) (M2.2) |
| end conc. lys (g/l) | 46.46 | 69.29 |
| ferm. time (h) | 30.5 | 30 |
| fermentation end volume (1) | 8.60 | 6.320 |
| reactor capacity (g lysine/h) | 13.1 | 14.6 |
| productivity (g lysine/l*1) | 1.51 | 2.303 |

There is a volumetric increase of productivity of 52.4% (from the calculation 2.303:1.51). The calculation, independent of the degree of filling, results in an increase in capacity of the reactor of 11.6% (from the calculation (14.6:13.1).

Figure 3A:
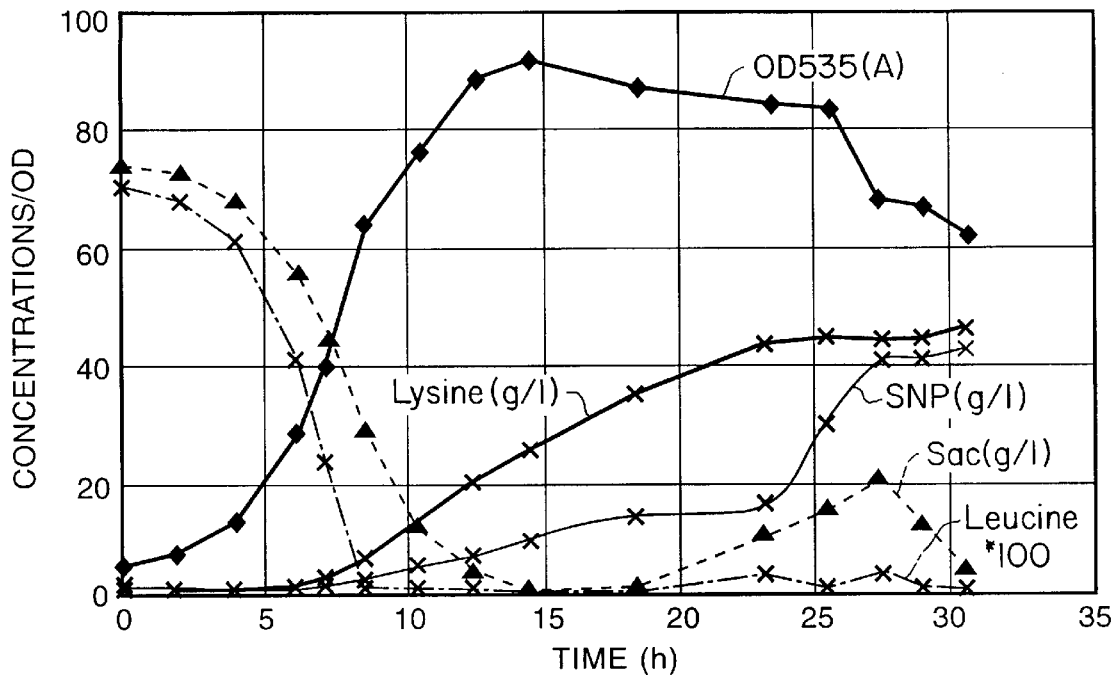
FIG. 3*a*. Timecourse of non-saccharose-limited fermentation (Base fermentation 941147).
Figure 3B:
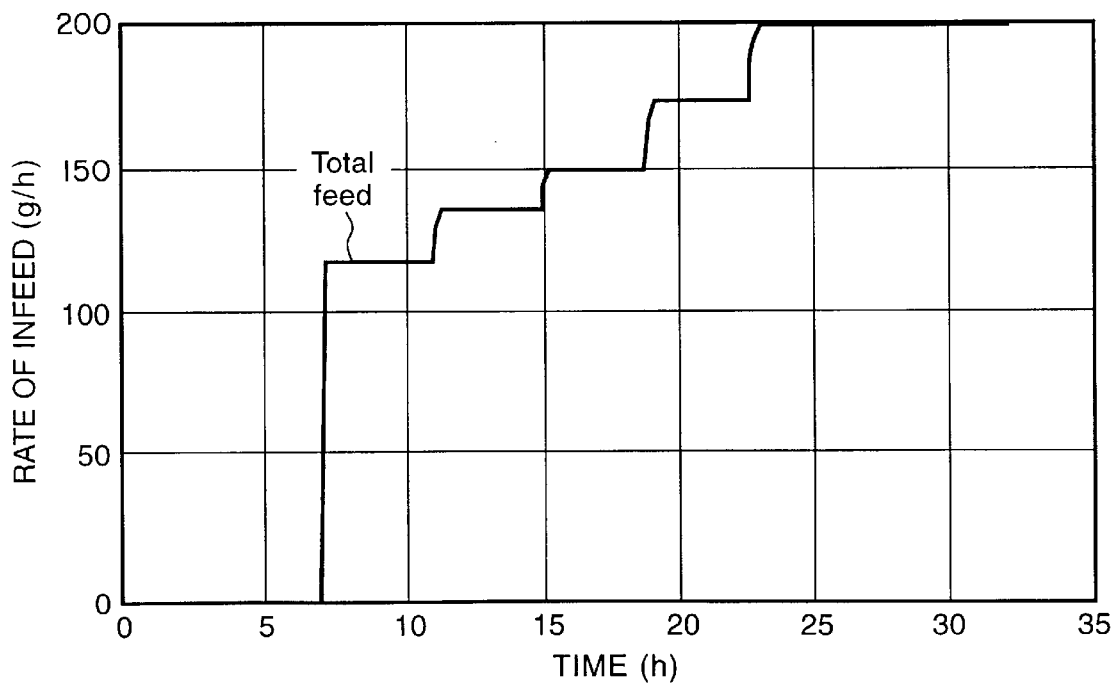
FIG. 3*b*. Rate of feed for non-saccharose-limited fermentation (Base fermentation 941147).
Figure 4A:
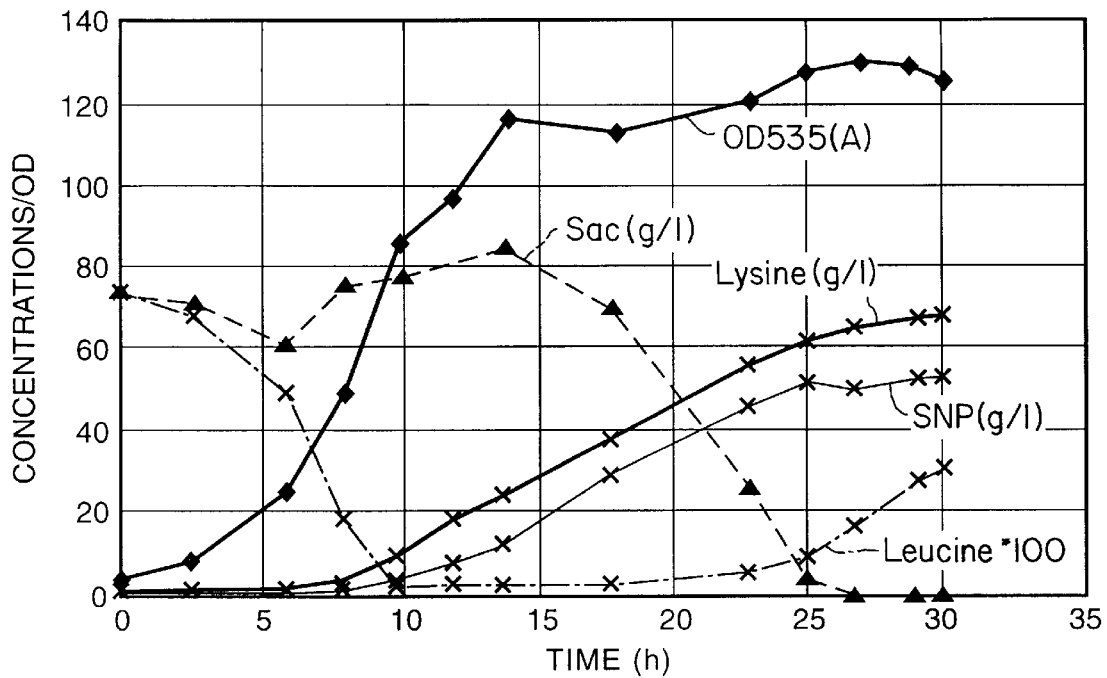
FIG. 4*a*. Timecourse of optimized fermentation (Optimized fermentation 941147).
Figure 4B:
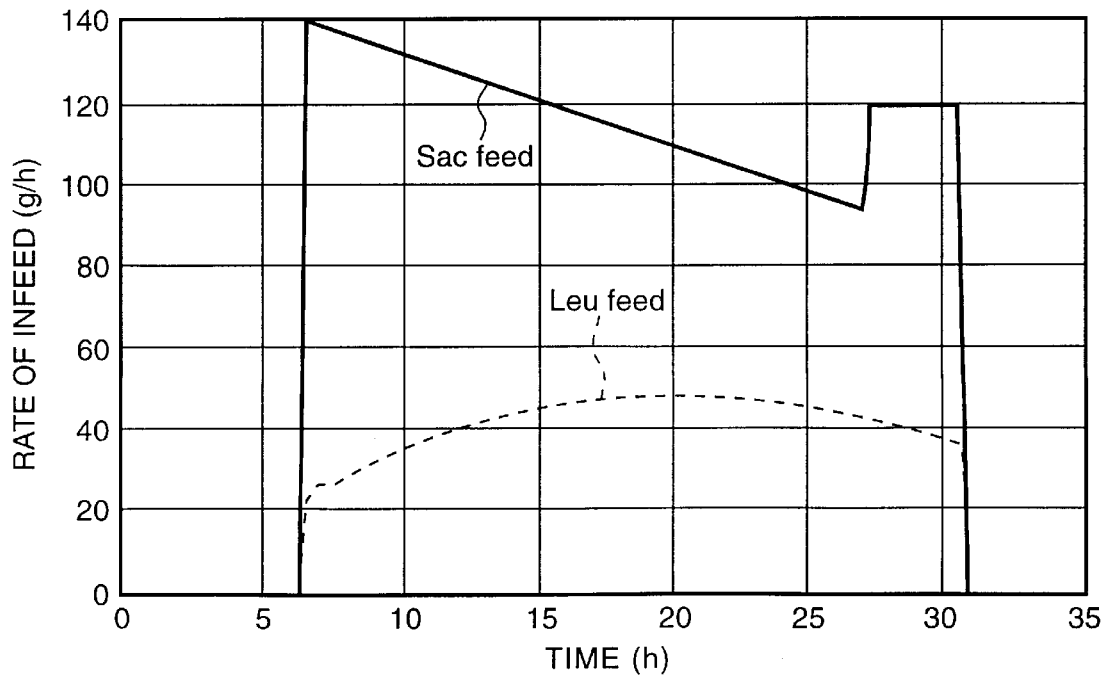
FIG. 4*b*. Rate of feed for optimized fermentation (Optimized fermentation 941147).

The figures show the courses of the fermentation and of the inflow currents (FIGS. 3a, 3b; FIGS. 4a, 4b).

What is claimed is:

1. A method of producing a target L-amino acid by fermenting a microorganism which excretes said target amino acid, said microorganism having an auxotrophy with respect to at least one limiting amino acid, wherein said method comprises charging a culture medium with a first inflow current containing said limiting amino acid and a second inflow current containing a carbon source necessary for the growth and formation of the target amino acid, wherein said inflow currents are initiated simultaneously but have chronological infeed profiles of differing forms.

2. The method according to claim 1, wherein the first inflow current has a profile which is exponential in a graphic representation vs. time and the second inflow current has a profile which is concave vs. time.

3. The method according to claim 1, wherein the first inflow current has a profile which is convex in a graphic representation vs. time, the second inflow current has a profile which is concave vs. time, and the profiles have different degrees of increase.

4. The method according to claim 1, wherein the first inflow current and the second inflow current have profiles which are convex in a graphic representation vs. time and the profiles have different degrees of increase.

5. The method according to claim 1, wherein the first inflow current has a profile which corresponds to a linearly falling line vs. time and the second inflow current has a profile which corresponds to a convex profile vs. time.

6. The method according to one of claims 1 to 5, wherein an L-amino acid selected from the group consisting of L-lysine,
L-methionine,
L-aspartate,
L-asparagine
L-isoleucine, and
L-threonine is produced.

7. The method according to claim 6, wherein L-lysine is produced using at least one amino-acid auxotrophic strain selected from the genera consisting of Corynebacterium, Brevibacterium, Arthrobacter, Microbacterium, Bacillus and Nacordia.

8. The method according to claim 7, wherein all of strains used are auxotrophic relative to at least one of the L-amino acids leucine, homoserine, threonine, methionine, isoleucine and/or exhibit resistance to at least one compound selected from the group consisting of L-lysine, lysine analogues, isoleucine, isoleucine analogues, threonine and threonine analogues.

9. The method according to claim 6, wherein a microorganism selected from the genera consisting of Corynebacterium, Brevibacterium, Arthrobacter, Microbacterium, Bacillus and Nacordia.

10. The method according to claim 9, wherein L-lysine is produced using at least one amino-acid auxotrophic strain selected from the genera consisting of Corynebacterium, Brevibacterium, Arthrobacter, Microbacterium, Bacillus and Nacordia.

11. The method according to claim 10, wherein a specific product formation rate of 0.06 $h^{-1}$ to 0.25 $h^{-1}$ is achieved.

12. The method according to claim 9, wherein the microorganism is selected from the species consisting of *Corynebacterium glutamicum, Brevibacterium flavum,* and *Brevibacterium lactofermentum.*

\* \* \* \* \*